United States Patent [19]

Blumenthal et al.

[11] Patent Number: 4,588,493

[45] Date of Patent: May 13, 1986

[54] HOT GAS MEASURING PROBE

[76] Inventors: Robert N. Blumenthal, 17470 Bard Ct., Brookfield, Wis. 53005; Andreas T. Melville, 204 N. 86th St., Milwaukee, Wis. 53226

[21] Appl. No.: 651,227

[22] Filed: Sep. 17, 1984

[51] Int. Cl.[4] ............................................. G01N 27/58
[52] U.S. Cl. ..................................... 204/410; 204/426; 204/428
[58] Field of Search ............... 204/428, 424, 425, 426, 204/427, 429, 15, 410

[56] References Cited

U.S. PATENT DOCUMENTS

| | | | |
|---|---|---|---|
| 3,454,486 | 7/1969 | Davies | 204/427 |
| 3,546,086 | 12/1970 | Sayles | 204/408 |
| 3,597,345 | 8/1971 | Hickam et al. | 204/427 X |
| 3,698,384 | 10/1972 | Jones | 204/410 X |
| 3,981,785 | 9/1976 | Sandler | 204/1 T X |
| 4,101,404 | 7/1978 | Blumenthal et al. | 204/428 |
| 4,186,072 | 1/1980 | Blumenthal et al. | 204/428 |
| 4,193,857 | 3/1980 | Bannister et al. | 204/428 |
| 4,290,586 | 9/1981 | Kane et al. | 266/80 |
| 4,319,966 | 3/1982 | Carlson et al. | 204/410 X |

FOREIGN PATENT DOCUMENTS

| | | | |
|---|---|---|---|
| 2304075 | 8/1974 | Fed. Rep. of Germany | 204/428 |
| 2401134 | 8/1974 | Fed. Rep. of Germany | 204/428 |
| 1296995 | 11/1972 | United Kingdom | 204/424 |
| 1442391 | 7/1976 | United Kingdom | 204/427 |

OTHER PUBLICATIONS

R. G. H. Record, Metallurgia and Metal Forming, Dec. 1972–Jan. 1973.
Y. L. Sandler, J. Electrochem. Soc., pp. 1378–1381, Aug. 1971.
R. G. H. Record, Instrument Practice, Mar. 1970.
Metals Handbook, pp. 466–488, vol. I, 8th. ed., (1961).

Primary Examiner—G. L. Kaplan
Attorney, Agent, or Firm—Fuller, House & Hohenfeldt

[57] ABSTRACT

An oxygen probe for measuring the characteristics of furnace gases. The probe includes electrodes of a long lasting and relatively inexpensive nickel containing alloy. The probe is formed with apertures and internal passages for ventilating the three phase contact zones between gas, electrolyte, and electrodes with furnace gases, thereby minimizing errors due to catalytic reactions at the electrodes. The probe sheath may be composed of the same alloy as the electrodes, and the electrodes may be fabricated as an integral part of the sheath, so that the sheath serves both as a structural member and as an electrical conductor for conducting voltage generated within the electrodes. A gas pump may be used to assure adequate ventilation to the electrode-electrolyte interfaces.

30 Claims, 10 Drawing Figures

HOT GAS MEASURING PROBE

BACKGROUND OF THE INVENTION

1. Field of the Invention

This invention pertains to measuring apparatus, and more particularly to apparatus for measuring gas characteristics.

2. Description of the Prior Art

The present invention is a further development of the subject matter of our U.S. Pat. Nos. 4,101,404 and 4,186,072.

It is well known to measure the oxygen content of gases by using a probe comprising a solid electrolyte which is in contact on one side with a known reference gas and on the opposite side with the gas whose oxygen content is to be measured. In such a probe, a voltage is generated between the two sides of the electrolyte. The magnitude of the voltage is dependent upon the temperature of the electrolyte and on the log of the ratio of the oxygen partial pressures on the opposing side of the electrolyte. This principle has been used in the past to measure the oxygen partial pressure of a hot furnace gas with various types of oxygen sensors, such as those disclosed in U.S. Pat. Nos. 3,454,486; 3,546,086; 3,597,345 and British Pat. No. 1,296,995.

The major components of all oxygen sensors are the electrolyte, the electrodes, i.e., anode, cathode, and the electrical lead wires which make electrical contact with the electrodes. The selection of a proper electrode material generally requires the satisfaction of chemical, electro-chemical, mechanical, and economical criteria. Platinum and other noble metals often meet the performance criteria, but they are very expensive. The specific electrode material and design are usually dependent on the particular environment to which it is subjected.

Commercial solid electrolyte oxygen sensors have been used in a wide variety of applications, such as motor vehicle exhaust, flue gas, molten copper or steel, and metal heat treating. As an example of the latter application, oxygen sensors are used for controlling the carbon potential in carburizing atmospheres. Control of Surface Carbon Content, *Metals Handbook*, Vol. 4, p. 417–431, 9th Edition, 1981. In addition to the aforementioned patents, oxygen sensors are disclosed in U.S. Pat. No. 4,193,857, German Pat. No. 2,401,134, and Australian Provisional Specification 47,828/79.

Although oxygen sensors have been used for several years and the principle of operation in those applications is quite simple, two major problems remain. The first is that the accuracy and repeatability of some commercial oxygen sensors are not high enough for heat treating applications requiring close carbon potential control. That is, the relationship between voltage, temperature, and percent carbon sometimes varies from sensor to sensor or with sensor usage. Carburizing and Carbonitriding, page 81, *American Society For Metals*, Metals Park, Ohio, 1977.

To accurately determine the oxygen partial pressure of the gaseous atmosphere in a heat treating furnace, the electrode in the furnace atmosphere (the anode) should maintain thermodynamic equilibrium between the oxygen activity within the atmosphere as a whole and the oxygen activity at the surface of the electrolyte. This condition is not always met in prior oxygen sensors.

The second major problem is that prior oxygen sensors have useful lives which are frequently limited because of anode or lead wire failures. Most failures are caused by chemical reactions between the electrodes and/or the lead wire and impurities in the furnace atmosphere. Even anodes made of noble metals such as platinum are susceptible to attack from contaminants such as zinc, silica, and sulphur.

Because platinum and other noble metals are expensive, and because anodes made from noble metals frequently have short useful lives, attention has been directed to other materials which might be suitable for anodes. Pure nickel, for example, has been used for anodes in fuel cells. However, although nickel possesses high temperature properties desirable in gas probes, it has been discovered that in heat treat atmospheres where the gases are not in equilibrium nickel acts as a catalyst which alters the gas composition locally which results in a nonrepresentative voltage output. Specifically, in heat treating atmospheres it has been found by our tests that the presence of nickel increases the rate of reaction of methane with water or carbon dioxide adjacent the anode surface. The altered gas composition generates a larger and non-representative voltage.

Other disadvantages of pure nickel electrodes are the formation of nickel oxide on the surface of the electrodes when exposed to an oxidizing atmosphere, and the formation of a low melting temperature nickel-sulphur eutectic when exposed to gases containing sulphur.

U.S. Pat. No. 4,193,857 indicates that certain nickel alloys may be useful as electrodes. However, the alloys disclosed in that patent are not entirely satisfactory either because the nickel content of the alloys disclosed is so high as to cause the aforementioned undesirable catalytic reactions, or because certain important alloying elements are lacking which render the electrode unable to meet all the design criteria. Heretofore it was not recognized in the art that metal electrodes catalyze reactions of the common enriching gases used for carburizing steel parts and thereby change the composition of the gas locally adjacent to the probe being measured and hence alter the output of the sensor and obtain distorted measurements by providing higher voltage readings. The common enriching gases include methane, propane and butane. The reason the nickel electrode sensor gave a higher emf reading was the catalytic reaction of the nickel electrode on the following reactions for example:

$$CH_4 + H_2O = CO + 3H_2$$

$$CH_4 + CO_2 = 2CO + 2H_2$$

(i.e., the rate of the reaction of $CH_4$ with $H_2O$ or $CO_2$ was increased and thus reduced the amount of $H_2O$ and $CO_2$ in the gas phase that was adjacent to the surface of the nickel electrode). This effect produced a lower oxygen potential at the electrode and therefore produced a larger emf.

Our tests have revealed that platinum anodes have also produced the above described catalytic reaction. Workers in the art have not recognized this catalytic reaction and the need to minimize the locally altered gas composition with adequate ventilation as subsequently described in detail. Several prior art probe constructions obstruct gas flow adjacent the anode with a packing or fill in the gas inlet passages to filter or prevent particulate debris from entering the probe. This teaching is contrary to the objectives of this invention and indicates that other workers in the art have not recognized the catalytic reaction described above and the resulting effect on the accuracy of a probe. An example of packing in the gas inlet is a probe sold by Barber-Colman which appears to be made in accordance with U.S. Pat. No. 4,193,857.

SUMMARY OF THE INVENTION

In accordance with the present invention, a long lasting hot gas measuring probe is provided which accurately and consistently measures the properties of gases without requiring the use of noble metals as the outer electrode or anode. This is accomplished by apparatus which includes electrodes composed of nickel, chromium and other selected elements to enhance carburization and oxidation resistance and minimize the undesirable catalytic reaction heretofore mentioned.

It has been discovered that electrodes made of nickel alloys containing about 35–60% nickel and certain other elements significantly improve the probe to provide long service life while having acceptably low catalytic effects in the zones of contact with the electrolyte. Thus, the nickel containing alloy electrodes enable accurate and repeatable measurements to be made by the probe, and the electrodes are considerably less expensive than the platinum or other noble metal electrodes formerly used. A preferred electrode range is an alloy containing about 35–45% nickel, 19–25% chromium, 43–18% iron, and 0.5–1.25% silicon. The relatively small amounts of silicon together with the chromium ranges disclosed herein form a stable oxide layer on the anode. The oxide layer minimizes penetration of carbon in the carburizing atmosphere into the parent metal. Carburization of the anode removes carbon from the gas adjacent anode which alters the gas locally and results in a lower and non-representive probe voltage. Also, if the carbon potential in the furnace atmosphere is lowered, then the reverse process can occur and the anode will give up carbon to enrich the local gas atmosphere resulting in a higher probe voltage.

It is known that thermodynamic equilibrium of the oxygen activity at the three phase contact zone of gas, electrode, and electrolyte is a necessary condition for obtaining a reversible oxygen electrode. Measurement accuracy and repeatability require that both the electrodes be reversible with respect to oxygen. In addition, the gas at the contact zone should be representative of the gas in the furnace for accurate readings. It has been discovered that good circulation and gas exchange of the gas adjacent to the anode with furnace gas is necessary for measurement accuracy and repeatability. Any reaction such as oxidation, reduction or carburization between the electrode and gas in addition to the aforementioned catalytic reaction could affect the local gas composition and give erroneous results. Accordingly, one embodiment of the present invention is designed with a configuration with a line contact between the electrolyte and electrode with suitable openings and grooves through which the gas to be measured continuously flows past the three phase contact zones. Theoretically, a point contact would be the optimum contact for exchange with the gas phase as disclosed in a paper printed in *The Journal of Electro-Chemical Society*, February, 1976, page 204–212. However, the contact resistance in such a commercial device would be too high for practical use and it would be difficult to mechanically maintain the geometry. Hence, line contact between the electrolyte and electrode as disclosed hereinafter, provides some of the advantages of a point contact in affording good ventilation and gas movement.

In one embodiment of the invention, the probe comprises a hollow cylindrical sheath closed at one end with a flat plate which serves as the anode. The sheath can be composed of the same material as the electrode plate, thereby eliminating the need for an electrical lead wire from the electrode to the probe electronic circuitry. The electrode plate contains a centrally located opening therethrough adapted to contact and support the ball nosed or hemispherical end of a tubular electrolyte. The electrolyte may be composed of stabilized or partially stabilized zirconia, as is known in the art. To provide adequate ventilation to the interface between the electrolyte and electrode at the zones of contact, the inside face of the electrode plate is constructed with several radial grooves, and the sheath wall contains numerous perforations. Hot gas is exchanged through the openings in the electrode plate, through the radial grooves, past the ball nosed end of the electrolyte, and through the sheath perforations. A cathode is inside the tubular electrolyte so as to contact the interior wall thereof opposite the external ball nose. Electrical lead wires connect the cathode with the remainder of the measuring circuitry in a known fashion. In a modified version, the flat end plate has a modified groove pattern. The sheath perforations are placed as closed as possible to the junction of the sheath wall and the end electrode plate. Adequate ventilation is provided to the zones of contact through the central opening and grooves and the nearby sheath perforations.

In a modified embodiment, the anode is disc-shaped with projecting converging walls which guide the flat end of tubular electrolyte to positively position the electrolyte over a central aperture in a flat portion. To provide adequate ventilation, the end of the electrode is fabricated with a central hole passing therethrough and several radial grooves in the inside face of the end wall. Additional holes may also be formed through the grooves. Gas passing through the holes and grooves flows between the corresponding portions of the electrolyte and electrode walls. This anode may be used in conjunction with a sheath of the same material or with a ceramic sheath.

In a further modification of the present invention, a perforated and closed ended ceramic sheath is utilized to hold a disc-shaped electrode adjacent the inside surface of the sheath closed end. The disc-shaped electrode and sheath end wall the communicating central holes therethrough. A stabilized or partially stabilized zirconia electrolyte having a ball nose at one end thereof is supported on the anode which also has radial grooves in the inside face thereof. A lead wire which may be of the same material as the anode is bonded thereto for conducting the generated voltage to the remainder of the control circuitry. The lead wire may be a large diameter wire or rod.

Most furnaces have fans which provide adequate circulation. A further modified embodiment provides a probe with a gas pump for use with a furnace which has poor circulation. In that situation, the ceramic or metal sheath is not perforated. Rather, the gas is drawn through the central opening in the end of the probe, through the radial grooves and past the electrolyte along the interior of the sheath, through a flow meter, a pump, and exhausted or returned back into the furnace in a closed loop.

It is known that a thermal emf can be generated in a hot gas probe when dissimilar metals are employed for the electrode lead wires. This can distort the results. It is not known whether the prior art ever employed compensating leads in an oxygen sensor as subsequently described.

Other objects and advantages of the invention will become apparent to those skilled in the art from the disclosure.

BRIEF DESCRIPTION OF THE DRAWINGS

FIG. 3 is a longitudinal sectional view of a modified embodiment of the present invention taken along line 3—3 of FIG. 3a.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
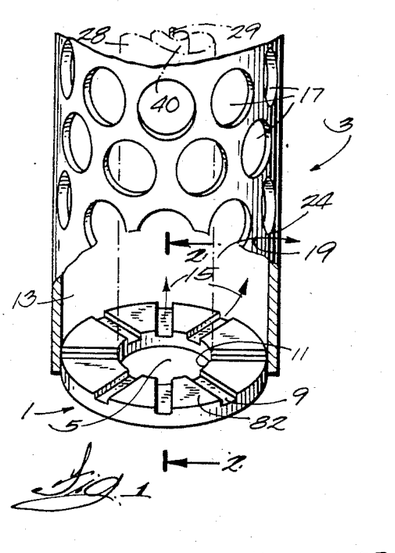
FIG. 1 is a partially broken-away perspective view of the second electrode portion or anode of the gas probe of the present invention.
Figure 2:
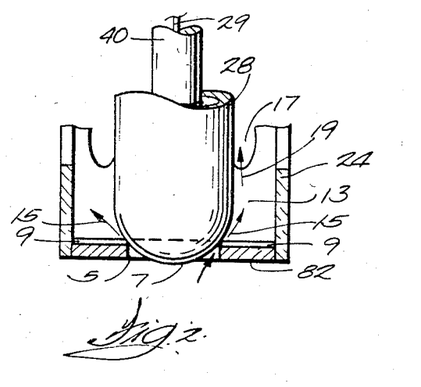
FIG. 2 is a partial sectional view taken along lines 2—2 of FIG. 1.

Referring to FIGS. 1 and 2, the gas contacting end 1 of a hot gas measuring probe 3 is illustrated. The general construction of the measuring probe 3 is disclosed in U.S. Pat. Nos. 4,101,404 and 4,186,072, both of which patents are hereby incorporated by reference into the present specification. As explained in U.S. Pat. Nos. 4,101,404 and 4,186,072, the hot gas measuring probe is mounted to the side wall of a furnace, not shown in FIGS. 1 and 2, with the gas contacting end inserted into the furnace for measuring the properties of the gas therein.

The hot gas measuring probe of the present invention includes a support tube or sheath 24 which can be fastened by a bracket to the furnace wall. To the gas contacting end 1 of the sheath is welded or otherwise permanently joined an end plate 82 which serves as the anode. The sheath and end plate 82 serve as a combined electrical conductor and electrode forming a portion of the apparatus for obtaining voltage measurements based on the thermodynamic properties of the furnace gas. The gas probe further includes a solid electrolyte tube 28 which can be composed of yttria stabilized zirconia. The electrolyte tube 28 contacts the end plate 82, as will be fully explained hereinafter. The other electrode or cathode 38 is inserted into the electrolyte tube 28 and can be held in place therein by a spring loaded ceramic rod 40, as is described in the aforementioned U.S. Pat. Nos. 4,101,404 and 4,186,072. The ceramic rod 40 includes one or more longitudinal bores 42, 99 for feeding a reference gas to the inside of the electrolyte tube and for receiving electrical lead wire 29 which conducts the voltage from the second electrode to the remainder of the instrument circuitry.

In accordance with the present invention, the sheath 24 and end plate or anode 82 are manufactured from a material which satisfies the mechanical, chemical, electro-chemical, and economical criteria for gas probe electrodes as described in the paper by Tedman, et al in *Journal of Electro Chemical Society*, Vol. 9, page 1170–1175, September, 1969. In addition, alloys are selected for the probe disclosed herein to minimize the catalytic reaction described above. As hereinafter disclosed, the nickel-chromium or iron nickel chromium alloy is relatively inexpensive and long lasting. The nickel content is sufficiently high so as to provide good mechanical properties at the high temperatures of heat treating furnaces. At the same time, the nickel content is low enough so that the undesirable catalytic reactions at the three phase contact points caused by nickel is not detrimental to measurement accuracy and repeatability. Acceptable results are obtained when the material is a nickel alloy containing about 35–60% nickel, but the preferred range is from about 35–45% nickel.

The criteria for an acceptable electrode or anode in accordance with the invention herein requires that the nickel alloy contain other important elements. Chromium, for example, is necessary for good mechanical properties at high temperatures. The chromium also promotes the formation of an adherent and protective oxide film. A particularly important element is silicon, because even a relatively small amount of silicon together with chromium aids in forming a more protective oxide coating on the anode with good carburization resistance. The oxide coating is very important for protecting the electrode because it provides both oxidizing and carburizing resistance for the parent metal. Satisfactory results are obtained with an alloy composed of about 35–60% nickel, 19–25% chromium, 43–14% iron, and 0.5–1.25% silicon. The preferred composition is 45% nickel, 25% chromium, 18% iron, 3% cobalt, 3% molybdenum, 3% tungsten, 1.5% manganese and 1.25% silicon. The preferred alloy for the anode 82 is available commercially under the trademarks RA333 and for the sheath 24 RA330. These trademarks are marks of Rolled Alloys of Temperance MI. The RA333 is more carburization resistant as well as meeting the other criteria. RA333 could also be used for the sheath but it is more expensive than RA330.

Further in accordance with the present invention, the hot gas probe 3 illustrated in FIG. 1 is designed so that the three phase contact points between the electrolyte, electrode, and the gas are adequately ventilated with fresh gas, thereby assuring that the gas measured is representative of the furnace gas. In addition, thermodynamic equilibrium with respect to oxygen is vital if the probe is to give accurate and consistent results. As illustrated in FIGS. 1 and 2, the electrode end plate 82 is fabricated with a central opening 5. The solid electrolyte 28 has a ball nosed outer surface 7 which fits within and is centrally supported by the electrode plate along the periphery of the opening 5. To permit adequate gas exchange around the contact line between the electrode plate and electrolyte, a series of grooves 9 extend radially from the central opening in the inside face of the electrode plate. Consequently, the contacts between the electrolyte and electrode plate are along arcuate lines 11 created at the junction of the inside face of the electrode plate and the circumferential surface of the central opening. Gas whose properties are to be measured by the probe of the present invention is exchanged with the furnace and can pass through the central opening, adjacent the contact lines between the electrode plate and electrolyte, through the grooves, and into the interior 13 of the sheath 24, as illustrated by arrows 15. To provide a return for the gas from the sheath interior 13, the sheath wall contains numerous perforations 17 through which the gas in the interior can flow back to the furnace, as illustrated by arrows 19. Alternatively, the gas can flow in the reverse direction or from either direction. It has been found that about 25-50% of the wall area of the sheath in the measuring region of the probe end should consist of perforations 17 where there is forced convection in the furnace because of a circulating fan. Thus, the zones of three phase contact between electrode, electrolyte, and gas, which occur along lines 11, are constantly supplied with fresh gas. As a result, the effect on probe accuracy and repeatability from undesirable catalytic reactions at the contact points which may be caused or enhanced by the nickel containing alloy electrode is minimized by the ventilation capability of the foregoing electrode or sheath configuration.

Prior measuring probes, such as those disclosed by U.S. Pat. No. 4,193,857 and German Pat. No. 2,401,134, include openings in the sheath in the region of the electrolyte-electrode interface. However, the prior devices failed to recognize the importance of rapid gas exchange to avoid local changes in composition caused by undesirable reactions described above.

Figure 3:
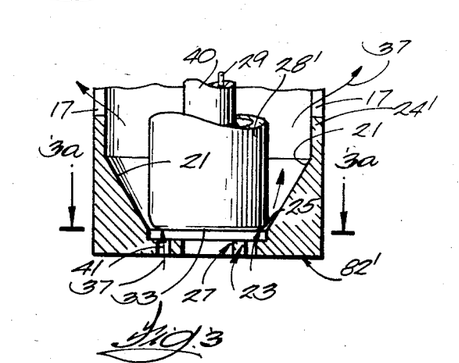
Figure 3A:
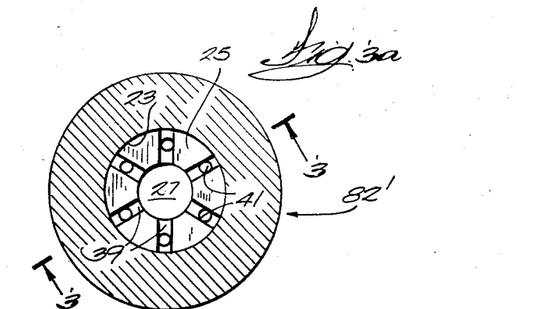
FIG. 3a is a sectional view of a modified embodiment.

Referring to FIGS. 3 and 3a, a modified embodiment of the present invention is shown. In FIGS. 3 and 3a, electrode 82' is formed as a closed end tube having an internal frusto-conical surface 21 which converges toward the end wall 23. The frusto-conical surface 21 terminates at a grooved flat surface 25 of end wall 23. The wall 23 has a central opening 27 therethrough and a series of grooves 39 which extend radially from the opening 27 in the inside face of the wall. The wall may also define small holes 41 extending therethrough and opening in the grooves. With the embodiment of FIGS. 3 and 3a, the electrolyte 28' is formed as a tube having a flat end 33 which contacts the inside face of the electrode wall. The outer diameter of the electrolyte tube 28' is slightly less than the diameter of the grooved flat surface 25 so as to be centrally guided by the tapered surface 21. The electrode 82' is manufactured from the nickel containing alloy previously described. The sheath 24' may be of the same nickel containing alloy, in which case the electrode 82' is preferably welded to the sheath.

Figure 4:
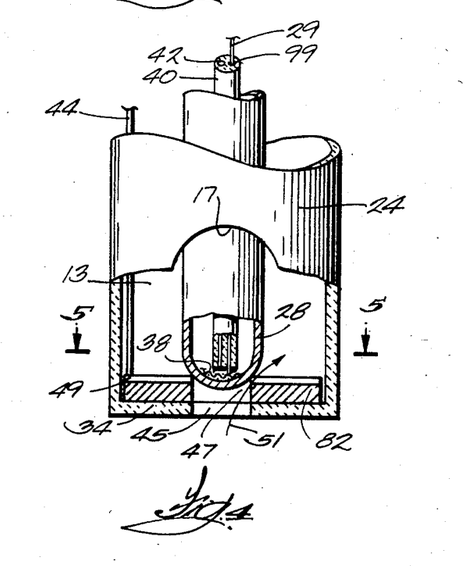
FIG. 4 is a side view, partially sectioned, of a further modified embodiment of the present invention.
Figure 4A:
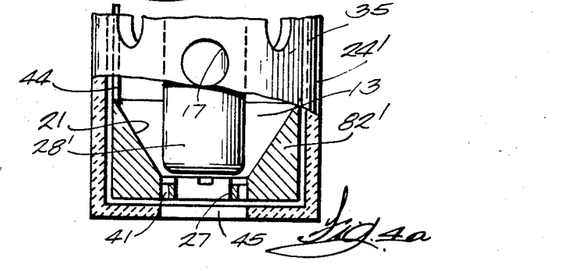
FIG. 4a is a side view of a further modified embodiment.

The sheath may also be of a ceramic material as illustrated in FIGS. 4 and 4a upon which the electrodes 82 and 82' are supported. If the sheath is made of ceramic, a lead wire 44 must be attached to the electrode for conducting the generated voltage to the remainder of the probe circuitry. Regardless of material, the wall 35 of sheath 24' has wall means defining preforations 17 which cover about 25-50% of the total wall area in the zone adjacent to the electrode or the region within about four inches of the electrode because the nickel containing alloy can cause the undesirable catalytic reaction. With the ceramic sheath the catalytic reaction is confined to the electrode area so the ventilation requirements are less. Thus, gas can flow or is exchanged, for example, through or from opening 27 and holes 41, along the grooves 39 and electrolyte end 33, through the annular space between the cylindrical surface 25 and outer surface of electrolyte tube 28', and out the sheath perforations, as indicated by arrows 37 which indicate gas exchange with the furnace atmosphere or in the reverse flow path.

Figure 5:
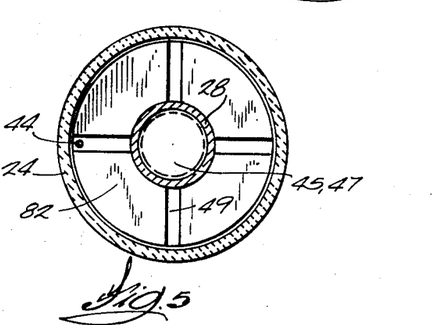
FIG. 5 is a sectional view taken along lines 5—5 of FIG. 4.

FIGS. 4, 4a and 5 illustrate a further modified embodiment of the present invention. The ceramic sheath disclosed in FIGS. 4, 4a, and 5 may be advantageous in high temperature applications. The ceramic sheath, however, is more subject to damage from thermal shock or mechanical stress. The metal alloy sheath is more durable and may be cheaper to manufacture. In FIGS. 4 and 5, the electrode or anode 82 is manufactured from the nickel alloy previously described in the shape of a disc. A lead wire 44 can be of the same nickel alloy as the electrode and is bonded to the electrode 82 for conducting the generated voltage to the remainder of the instrument circuit. The electrode 82 rests in contact with the end wall 34 of ceramic sheath 24. The wall 34 and electrode disc 82 contain central apertures 45 and 47, respectively, and the ball nosed end of electrolyte 28 is centrally guided in the aperture 47. The face of the electrode opposite the sheath wall 34 contains a series of radial grooves 49 extending from the disc aperture 47. Thus, gas flows through the apertures 45 and 47, past the ball nosed end of electrolyte 28, through grooves 49, to the interior of the sheath, and out the perforations 17, as indicated by arrows 51 or in a reverse flow path. FIG. 4a is a modified embodiment in which the flat end of the electrolyte tube 28' is guided into position against the flat area 25 by the taper in the anode converging walls 21.

Figure 6:
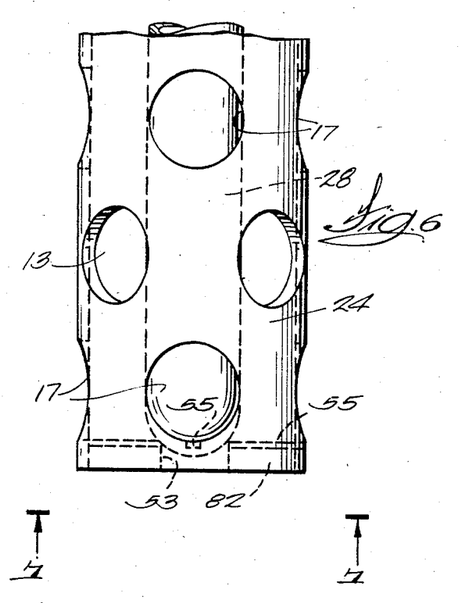
FIG. 6 is a side view of a further modified embodiment of the present invention.
Figure 7:
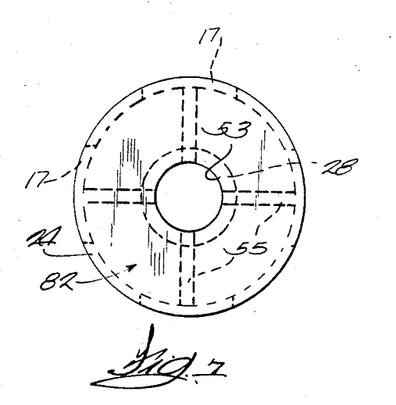
FIG. 7 is a view taken along lines 7—7 of FIG. 6.

FIGS. 6 and 7 depict another modified embodiment of the present invention which is especially useful in miniature probes. The electrode 82 and sheath 24 are made of the nickel containing alloy described previously, and they are welded or otherwise permanently joined. The electrode 82 has a central opening 53 into which the zirconia electrolyte 28 is placed. The inside face of the electrode 82 is radially grooved, as at 55. The sheath perforations 17 are located in the sheath wall as close as possible to the electrode. Gas flows through the opening 53, grooves 55, and perforations 17 in a manner substantially similar to that previously explained.

Figure 8:
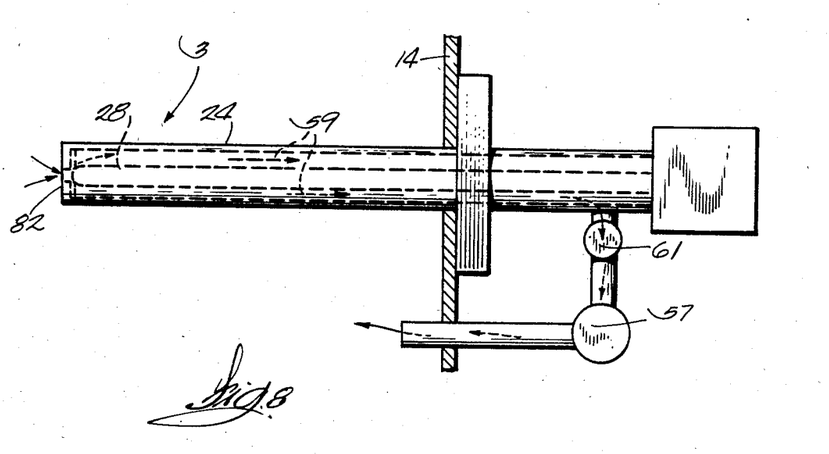
FIG. 8 is a schematic view of a further modified embodiment of the present invention.

In some instances, the circulation of gas within the furnace may be insufficient to adequately ventilate the three phase contact points. In that situation, a gas pump may be employed to assure adequate ventilation. FIG. 8 schematically illustrates a gas probe 3 mounted to a port 14 in a furnace wall. Any of the previously described electrode, sheath, and electrolyte combinations may be utilized with a pump. However, in all cases, the walls of the sheath 24 are not perforated. Gas is drawn through the respective openings in the electrode and past the three phase contact point between the electrode and electrolyte 28 and along the interior of the sheath to the pump 57, as illustrated by arrows 59. From the pump, the gas can be either discharged for remote disposal or may be returned to the furnace. A flow meter 61 with a valve is desirable to control flow rate. A pump can be employed with probe constructions as described in U.S. Pat Nos. 4,101,404 and 4,186,072 with an axial opening rather than in the side walls.

To compensate for any thermal emf generated because of the use of dissimilar metals for the lead wire 29 and lead wire 44 or sheath 24 the lead wire 29 should be selected so that it will compensate for any thermal emf. With the nickel containing alloy ranges disclosed 30–40% rhodium and the balance platinum alloy wire has provided satisfactory results when used for the inner electrode lead wire 29. The preferred lead wire for use with the preferred alloy is 70% platinum and 30% rhodium.

Thus, it is apparent that there has been provided, in accordance with the invention, an oxygen measuring probe which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and the broad scope of the appended claims.

We claim:

1. In an oxygen sensor for measuring the properties of a gas inside a furnace having a solid electrolyte means with an interior surface and an exterior surface; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, the improvement wherein:
a. said second electrode is unitarily connected to the sheath means to substantially close one end thereof;
b. said sheath means being an electrical conductor to enable the sheath means to conduct the voltage from the second electrode;
c. said second electrode and said electrolyte having co-operating wall means defining gas passages to allow passage of gas past the points of contact of the second electrode and said electrolyte and into the interior of the sheath means, said cooperating wall means providing a line contact of non-noble metal electrode and electrolyte, and said gas passages affording adequate gas exchange at the line contact between the electrolyte and second electrode to minimize chemical reactions and provide representative measurements.

2. The improvement of claim 1 wherein the sheath means and second electrode are comprised of an alloy consisting essentially of 35–60% nickel, 19–25% chromium, 43–14% iron, and 0.5–1.25% silicon.

3. The improvement of claim 1 wherein the alloy consists of about 45% nickel, 25% chromium, 3% cobalt, 3% molybdenum, 3% tungsten, and 1.25% manganese, 1.25% silicon and balance iron.

4. The improvement of claim 1 wherein said second electrode has a central opening and wherein:
a. said electrolyte is fabricated as a tube having a ball nose on the exterior surface of one end, the ball nose end being adapted to contact the second electrode around the periphery of the central opening; and
b. said second electrode defines a plurality of grooves in the inside face thereof extending radially from the central opening,
so that the electrolyte contacts the second electrode around a plurality of arcuate lines to form the line contact and to permit gas exchange through the second electrode central opening, past the electrolyte ball nose, and through the sheath means perforations, thereby ventilating the line contact between the second electrode and the electrolyte.

5. The improvement of claim 1 wherein the perforations in the sheath means constitute about 25–50% of the area of the sheath near the second electrode.

6. The improvement of claim 1 wherein said co-operating wall means provide an annular line contact with at least one interruption in the line at a gas passage.

7. The improvement of claim 1 wherein said second electrode has a central aperture located at one end of said electrolyte tube.

8. The improvement of claim 1 wherein the second electrode and wire lead are made from an alloy consisting of about 35% nickel, 19% chromium, 1.25% silicon and the balance iron.

9. In an oxygen sensor for measuring the properties of a gas inside a furnace having a solid electrolyte means with an interior surface and an exterior surface; a first electrode in contact with the interior surface of the electrolyte; a second electrode having a surface in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, the improvement wherein:
a. the electrolyte is in the form of a tube having a flat end on the exterior surface and adapted to contact the second electrode;
b. the second electrode defines a frusto-conical interior surface terminating in a grooved flat adapted to guide the electrolyte and a central opening in said electrode flat; and
c. the second electrode defining a plurality of grooves in the inside face thereof and extending radially from the central opening,
so that the gas may be exchanged with the interior of the sheath by flow to, through or from the central opening, through the grooves, and past the electrolyte to the interior of the sheath means thereby ventilating the points of contact between the electrolyte and second electrode.

10. The improvement of claim 9 wherein the sheath is constructed of ceramic material.

11. In an oxygen sensor for measuring the properties of a gas inside a furnace having a solid electrolyte with an interior surface and an exterior surface; a first electrode in contact with the electrolyte interior surface; a second electrode in contact with the electrolyte exterior surface;

conductor means for conducting voltage generated between the first and second electrodes corresponding to the gas properties; and sheath means for supporting and protecting the electrolyte and electrodes having a wall defining an interior chamber closed at one end by an end wall,
the improvement wherein:

a. the second electrode is shaped as a substantially solid flat disc having an inside face located opposite the end wall of the sheath means and in contact with the electrolyte, the disc electrode being made from a material consisting essentially of 35–60% nickel, 19–25% chromium, 43–14% iron, and 0.5–1.25% silicon, the disc having a central opening therethrough and at least one groove extending radially from the central opening in the inside face of the disc;

b. an electrically conducting lead wire is joined to the inside face of the disc, the lead wire being composed of an alloy having a composition consisting essentially of 35–60% nickel, 19–25% chromium, 43–14% iron, and 0.5–1.25% silicon;

c. the electrolyte is formed with a ball nosed end adapted to contact the periphery of the electrode disc central opening along a plurality of arcuate lines;

d. the end wall of the sheath means defines an opening which communicates with the central opening of the electrode disc; and e. the sheath means wall defines a plurality of perforations, so that the gas within the furnace flows through the openings in the sheath means end wall and disc electrode, past the electrolyte, and in or out the sheath perforations, thereby minimizing catalytic chemical reactions at the second electrode.

12. The improvement of claim 11 wherein the perforations constitute approximately 25–50% adjacent the second electrode.

13. The improvement of claim 11 wherein the sheath means is made from Ceramic.

14. The improvement of claim 11 wherein the disc electrode and wire lead are made from an alloy consisting of about 35% nickel, 19% chromium, 1.25% silicon and the balance iron.

15. In an oxygen sensor for measuring the properties of a gas inside a furnace having a solid electrolyte with an interior surface and an exterior surface; a first electrode in contact with the electrolyte interior surface; a second electrode in contact with the electrolyte exterior surface;

conductor means for conducting voltage generated between the first and second electrodes corresponding to the gas properties; and sheath means for supporting and protecting the electrolyte and electrodes having a wall defining an interior chamber closed at one end by an end wall, the improvement wherein:

a. the second electrode is shaped as a substantially solid flat disc having an inside face located opposite the end wall of the sheath means and in contact with the electrolyte;

b. an electrically conducting lead wire is joined to the inside face of said disc, the lead wire of an alloy having a composition consisting essentially of 35–60% nickel, 19–25% chromium, 43–14% iron, and 0.5–1.25% silicon;

c. the electrolyte is formed with a ball nosed end adapted to contact the periphery of the electrode disc central opening along a plurality of arcuate lines;

d. the end wall of the sheath means defines an opening which communicates with the central opening of the electrode disc; and e. the sheath means wall defines a plurality of perforations, so that the gas within the furnace flows through the openings in the sheath means end wall and disc electrode, past the electrolyte, and in or out the sheath perforations, thereby minimizing catalytic chemical reactions at the second electrode.

16. In an oxygen sensor for measuring the properties of a gas within a furnace having sheath means with an imperforate wall defining an interior chamber, the sheath means having a first end inserted inside the furnace and a generally closed second end extending outside the furnace; first and second electrodes located within the sheath means chamber, a solid electrolyte interposed between and in contact with the electrodes to define a gas, electrode and electrolyte interface; and conductor means for conducting voltage generated within the electrodes in response to selected gas characteristics, and wherein:

a. the first electrode is formed as an end wall for permanently closing the first end of the sheath means;

b. the first electrode has wall means defining at least one opening therethrough to permit furnace gases to flow to the sheath means interior chamber and to and from said interface; and including c. pump means connected to the second end of the sheath means for drawing furnace gas through the opening in the first electrode, into the sheath means interior chamber, and out of the second end of the sheath means, and to and from said gas, electrode, and electrolyte interface, so that the electrodes and electrolyte are constantly ventilated with fresh furnace gas to minimize catalytic reactions at said interface and provide a representative measurement.

17. The improvement of any of claims 1, 9, 11 and 16 wherein said lead wire is selected from an alloy to compensate for any EMF generated because of dissimilar metals employed as leads and electrodes.

18. The improvement of claim 17 in which said compensating lead is 30–40% rhodium and the balance platinum.

19. In an oxygen sensor for measuring the properties of a gas inside a furnace having a solid electrolyte with an interior surface and an exterior surface; a first electrode in contact with the electrolyte interior surface; a second electrode in contact with the electrolyte exterior surface; conductor means for conducting voltage generated between the first and second electrodes corresponding to the gas properties; and sheath means for supporting and protecting the electrolyte and electrodes and said sheath means having a wall defining an interior chamber closed at one end by an end wall, the improvement wherein:

a. the second electrode is in the shape of a disc and made from an alloy consisting essentially of 35–60% nickel, 19–25% chromium, 43–14% iron, and 0.5–1.25% silicon, the disc having a central opening therethrough and at least one groove extending radially from the central opening in the inside face of the disc;

b. the end wall of the sheath means defines an opening which communicates with the central opening of the electrode disc; and c. the sheath means wall defines a plurality of perforations, so that the gas within the furnace flows through the openings in the sheath means and wall and disc electrode, past the electrolyte, and out the sheath means perforations, thereby minimizing catalytic chemical reactions at the second electrode:

20. The improvement of claim 19 wherein the disc electrode and wire lead are made from an alloy consisting of about 45% nickel, 25% chromium, 3% cobalt, 3% molybdenum, 3% tungsten, 1.25% manganese, and 1.25% silicon and the balance iron.

21. The improvement of claim 19 wherein the disc electrode and wire lead are made from an alloy consisting of about 35% nickel, 19% chromium, 1.25% silicon and the balance iron.

22. The improvement of claim 19 including wall means in said sheath defining openings, said openings comprising at least 25% of said sheath means adjacent said second electrode, said openings affording ventilation to provide gas exchange at said contact between the electrode and electrolyte to provide representative measurements.

23. An oxygen sensor for measuring the properties of gas inside a furnace having a solid electrolyte with an interior surface and an exterior surface; a first electrode in contact with the electrolyte interior surface; a second electrode in contact with the electrolyte exterior surface; conductor means for conducting voltage generated between the first and second electrodes corresponding to the gas properties; and sheath means for supporting and protecting the electrolyte and electrodes having a wall defining an interior chamber closed at one end by an end wall, and wherein:
the second electrode is made from an alloy consisting of about 45% nickel, 25% chromium, 3% cobalt, 3% molybdenum, 3% tungsten, 1.25% manganese, and 1.25% silicon and the balance iron.

24. An oxygen sensor for measuring the properties of a gas inside a furnace having a solid electrolyte with an interior surface and an exterior surface; a first electrode in contact with the electrolyte interior surface; a second electrode in contact with the electrolyte exterior surface; conductor means for conducting voltage generated between the first and second electrodes corresponding to the gas properties; and sheath means for supporting and protecting the electrolyte and electrodes having a wall defining an interior chamber closed at one end by an end wall, and wherein:
the second electrode is made from an alloy consisting of about 35% nickel, 19% chromium, 1.50% manganese, and 1.25% silicon and 0.05% carbon and the balance iron.

25. An oxygen sensor for measuring the properties of a gas inside a furnace having a solid electrolyte means with an interior surface and an exterior surface; a first electrode in contact with the interior surface of the electrolyte; a second electrode having a surface directly in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace,
and wherein:
a. said second electrode is unitarily connected to the sheath means to substantially close one end thereof;
b. said sheath means being an electrical conductor to enable the sheath means to conduct the voltage from the second electrode;
c. said second electrode and said electrolyte having co-operating wall means defining gas passages to allow passage of gas past the points of contact of the second electrode and said electrolyte and into the interior of the sheath means, said cooperating wall means providing a line contact of non-noble metal electrode and electrolyte, and said gas passages affording adequate gas exchange at the line contact between the electrolyte and second electrode to minimize chemical reactions and provide representative measurements and wherein the sheath means and second electrode are made from an alloy consisting essentially of 35–60% nickel, 19–25% chromium, 43–14% iron, and 0.5–1.25% silicon.

26. In an oxygen sensor for measuring the properties of a gas inside a furnace having a solid electrolyte with an interior surface and an exterior surface; a first electrode in contact with the electrolyte interior surface; a second electrode in contact with the electrolyte exterior surface; conductor means for conducting voltage generated between the first and second electrodes corresponding to the gas properties; and sheath means for supporting and protecting the electrolyte and electrodes having a wall defining an interior chamber closed at one end by an end wall, the improvement wherein:
a. the second electrode is shaped as a substantially solid flat disc having an inside face located opposite the end wall of the sheath means and in contact with the electrolyte, the disc electrode being made from an alloy consisting essentially of 35–60% nickel, 19–25% chromium, 43–14% iron, and 0.5–1.25% silicon, the disc having a central opening therethrough and at least one groove extending radially from the central opening in the inside face of the disc;
b. an electrically conducting lead wire is joined to the inside face of the disc, the lead wire being composed of an alloy consisting essentially of 35–60% nickel, 19–25% chromium, 14–43% iron, and 0.5–1.25% silicon;
c. the electrolyte is formed with a ball nosed end adapted to contact the periphery of the electrode disc central opening along a plurality of arcuate lines;
d. the end wall of the sheath means defines an opening which communicates with the central opening of the electrode disc; and
e. the sheath means wall defines a plurality of perforations,
so that the gas within the furnace flows through the openings in the sheath means end wall and disc electrode, past the electrolyte, and in or out the sheath perforations, thereby minimizing catalytic chemical reactions at the second electrode.

27. An oxygen sensor for measuring the properties of a gas inside a furnace having a solid electrolyte means with an interior surface and an exterior surface; a first electrode in contact with the interior surface of the electrolyte; a second electrode having a surface directly in contact with the exterior surface of the electrolyte; conductor means for conducting a voltage generated between the first and second electrodes in correspondence with gas properties; and sheath means having a generally tubular wall surrounding the electrodes and electrolyte for supporting the electrodes and electrolyte within the furnace, and wherein:
a. said second electrode is unitarily connected to the sheath means to substantially close one end thereof;
b. said sheath means being an electrical conductor to enable the sheath means to conduct the voltage from the second electrode;
c. said second electrode and said electrolyte having co-operating wall means defining gas passages to allow passage of gas past the points of contact of the second electrode and said electrolyte and into the interior of the sheath means, said cooperating wall means providing contact of non-noble metal electrode and electrolyte, and said gas passages affording adequate gas exchange at the contact between the electrolyte and second electrode to minimize chemical reactions and provide representative measurements and wherein the sheath means and second electrode are comprised of an alloy consisting essentially of 35–60% nickel, 19–25% chromium 43–14% iron, and 0.5–1.25% silicon.

28. The improvement of claim 27 including wall means in said sheath defining openings, said openings comprising at least 25% of said sheath means adjacent said second electrode, said openings affording ventilation to provide gas exchange at said contact between the electrode and electrolyte to provide representative measurements.

29. In an oxygen sensor for measuring the properties of a gas inside a furnace having a solid electrolyte with an interior surface and an exterior surface; a first electrode in contact with the electrolyte interior surface; a second electrode in contact with the electrolyte exterior surface; conductor means for conducting voltage generated between the first and second electrodes corresponding to the gas properties; and sheath means for supporting and protecting the electrolyte and electrodes having a wall defining an interior chamber closed at one end by an end wall, and wherein the second electrode is shaped as a substantially solid flat disc having an inside face located opposite the end wall of the sheath means and in contact with the electrolyte, the disc electrode being made from an alloy consisting essentially of 35–60% nickel, 19–25% chromium, 43–14% iron, and 0.5–1.25% silicon;

and wherein, the sheath means wall defines a plurality of perforations, so that the gas within the furnace flows through the openings in the sheath means past the electrolyte, and in or out the sheath perforations, thereby minimizing catalytic chemical reactions at the second electrode.

30. The improvement of claim 29 including wall means in said sheath defining openings, said openings comprising at least 25% of said sheath means adjacent said second electrode, said openings affording ventilation to provide gas exchange at said contact between the electrode and electrolyte to provide representative measurements.

* * * * *